United States Patent [19]

Zoeller et al.

[11] Patent Number: 5,144,067
[45] Date of Patent: Sep. 1, 1992

[54] PROCESS FOR THE COPRODUCTION OF ALKYL IODIDES AND ALPHA-IODOCARBOXYLIC ACIDS AND/OR ANHYDRIDES THEREOF

[75] Inventors: Joseph R. Zoeller; Michael R. Cushman, both of Kingsport, Tenn.; Regina M. Moncier, Bristol, Va.; Brent A. Tennant, Kingsport, Tenn.

[73] Assignee: Eastman Kodak Company, Rochester, N.Y.

[21] Appl. No.: 414,239

[22] Filed: Sep. 29, 1989

[51] Int. Cl.$^5$ .................. C07C 27/00; C07C 51/00
[52] U.S. Cl. .................. 562/479; 562/496; 562/507; 562/602; 562/603; 562/887; 562/888; 570/196; 570/197; 570/252; 570/253; 570/201
[58] Field of Search .............. 562/888, 887, 479, 496, 562/507, 602, 603; 570/141, 142, 201, 196, 197, 252, 253

[56] References Cited

U.S. PATENT DOCUMENTS

| | | |
|---|---|---|
| 3,647,893 | 3/1972 | Silbert et al. . |
| 3,652,682 | 3/1972 | Silbert .................. 570/142 |
| 3,666,820 | 5/1972 | Silbert . |
| 3,716,592 | 2/1973 | Silbert et al. . |

FOREIGN PATENT DOCUMENTS 86-7389  9/1986  South Africa .

OTHER PUBLICATIONS

Silbert, et al, J. Org. Chem., 33, 3670 (1968).
Silbert, J. Am. Oil Chemists Soc., 46, 615 (1969).
Burger; Alfred: *Medicinal Chemistry*, 2nd Edition, p. 36, 1964.

Primary Examiner—Marianne M. Cintins
Assistant Examiner—Margaret Argo
Attorney, Agent, or Firm—J. Frederick Thomsen; William P. Heath, Jr.

[57] ABSTRACT

Disclosed is a process for the coproduction of (1) an alkyl iodide and (2) an α-iodocarboxylic acid, a mono-α-iodocarboxylic anhydride or a mixture thereof which comprises contacting a mixture of an iodine compound and a carboxylic anhydride with a peroxide at an elevated temperature.

9 Claims, No Drawings

PROCESS FOR THE COPRODUCTION OF ALKYL IODIDES AND ALPHA-IODOCARBOXYLIC ACIDS AND/OR ANHYDRIDES THEREOF

This invention concerns a novel process for the coproduction of an alkyl iodide and an α-iodocarboxylic acid and/or a mono-α-iodocarboxylic anhydride. More specifically, this invention concerns the reaction of a mixture of a carboxylic acid anhydride and an iodine compound, or a mixture of a carboxylic acid, a carboxylic anhydride and an iodine compound, with a peroxide at elevated temperature.

The literature contains numerous references to uses of α-iodocarboxylic acids and derivatives thereof, primarily in the biological arts. For example, the tumor inhibiting properties of iodoacetic acids and esters thereof are described by M. S. Rheins, J. A. Filppi, and V. S. Moore, Cancer Res., 35, 1514 (1975) and F. S. Liotti and P. Locci, Boll. Ist. Serioter. Milan., 65, 61 (1986). The prophylactic effect of α-iodoacetic acid esters in the prevention of parasitic infections by Schistosomiasis Japonica is described by F. Bai, Z. Leng, H. Ying, R. Wang, S. Zou, and X. Gu, Yaoxue Xuebao, 16, 621 (1981). There are several other industrial uses for α-iodocarboxylic acids and esters. For example, the use of α-iodocarboxylic acids and their esters, especially iodoacetic and α-iodopropanoic acids, in the manufacture of antibacterial plywood is described in Japanese Pat. No. 82-92,076. The use of iodoacetic acid as an image stabilizer in silver halide photographic processing is disclosed in Japanese Pat. Nos. 74-81,033 and 86-112,145. The α-iodocarboxylic acids also are useful chemical intermediates for the preparation of a wide variety of α-substituted carboxylic acids, for example, by the reaction thereof with various nucleophiles.

Alkyl iodides have been used extensively in organic syntheses as alkylating agents, for example, in the alkylation of nitrogen-containing compounds and in the preparation of ethers. Alkyl iodides, especially methyl iodide, are used in large volumes in carbonylation processes such as, for example, the rhodium-catalyzed carbonylation of alkanols and alkyl esters to obtain carboxylic acids and/or carboxylic anhydrides.

Halogenation of carboxylic acids with iodine has been rare and, for the most part, the synthesis of iodocarboxylic acids has been limited to exchanging iodide for either chlorine or bromine in preformed halogenated materials. See, for example, J. B. Conant and W. R. Kirner, J. Am. Chem. Soc., 46, 232 (1924); J. B. Conant and R. E. Hussey, J. Am. Chem. Soc., 47, 476 (1925); and J. B. Conant, W. R. Kirner, and R. E. Hussey, J. Am. Chem. Soc., 47, 488 (1925). Other methods using molecular iodine have been devised, although each entails some method of circumventing the thermodynamic problems associated with the formation of hydrogen iodide. These methods include the reaction of the carboxylic acid dianions (generated using lithium N-isopropylcyclohexylamide) with iodine [M. W. Rathke and A. Lindert, Tet. Lett., 3995 (1971)], the generation of α-iodoacyl chlorides from the reaction of acyl chlorides with iodine in thionyl chloride [D. N. Harpp, L. Q. Bao, C. J. Black, J. G. Gleason, and R. A. Smith, J. Org. Chem., 40, 3420 (1975)] and iodination with iodine in the presence of cupric ($Cu^{2+}$) salts [C. A. Horiuchi and J. Y. Satoh, Chem. Lett., 1509 (1984)]. The first method is impractical due to the expensive strong bases required and the latter two require a secondary oxidation to force the reaction. In the case of the thionyl chloride procedure, thionyl chloride and the hydrogen iodide coproduct are converted to iodine and sulfur. In the cupric salt-induced iodinations, $Cu^{2+}$ is reduced to $Cu^{1+}$ and the copper salts must be removed by filtration. Russian Pat. No. 321,103 (1975) describes the reaction of iodine with ketene and the subsequent isolation of iodoacetic anhydride. This reaction presumably involves the addition of iodine to the olefinic portion of ketene.

Silbert and co-workers have demonstrated the feasibility of generating alkyl and aryl iodides from diacyl or alkyl-acyl peroxides in carboxylic acid solutions containing molecular iodine. See L. S. Silbert, D. Swern, and T. Asahara, J. Org. Chem., 33, 3670 (1968) and references cited therein; L. S. Silbert, J. Am. Oil Chemists Soc., 46, 615 (1969) and references cited therein; and L. S. Silbert, U.S. Pat. Nos. 3,647,893, 3,652,682, 3,666,820 and 3,716,592. These references do not describe the formation of α-iodocarboxylic acids. It is also generally known that the addition of hydrogen peroxide to carboxylic anhydrides ultimately generates the corresponding diacyl peroxide [L. F. Martin, Organic Peroxide Technology, Noyes Data Corporation, Park Ridge, N.J., pages 222–225 (1973)] and that diacyl peroxides thermally degrade to form carbon dioxide and a radical of one carbon atom less than the carboxylic anhydride precursor [J. March, Adv. Org. Chem., John Wiley & Sons, New York, NY, 3rd edition, p.168 (1985) and references cited therein]. A detailed description of the decomposition of diacetyl peroxide is described by M. Swarc in Peroxide Reaction Mechanisms, J. O. Edwards, ed., John Wiley & Sons, Inc., New York, NY, p. 153 (1962).

According to European patent application no. 217,191 and South African Pat. No. 86/7389, iodine-containing contaminants may be removed from carbonylation effluents by contacting the effluents with peroxides. However, these references do not identify either the reactant or reactants involved in the process or the products obtained therefrom.

According to our invention there is provided a process for the coproduction of (1) an alkyl iodide and (2) an α-iodocarboxylic acid, a mono-α-iodocarboxylic anhydride or a mixture thereof by contacting a mixture of an iodine compound and a carboxylic anhydride with a peroxide at an elevated temperature. The alkyl iodide produced contains one less carbon atom than the carboxylic acid moiety of the anhydride employed. The reaction represents an example of a radical-induced equilibrium reaction. Hence, the proportion of products (1) and (2) recoverable from the process depends on the conditions employed and the particular mode used in the operation of the process.

The iodine compounds which may be used in our novel process include molecular iodine ($I_2$), inorganic iodides such as iodide salts, e.g., alkali metal and alkaline earth metal iodides, carboxylic acid iodides and organic iodine compounds wherein an iodine atom is covalently bonded to a non-aromatic carbon atom, i.e., aliphatic and cycloaliphatic iodine compounds. The preferred iodine-containing reactants are carboxylic acid iodides, which are generated in situ from the interaction of hydrogen iodide with carboxylic acid anhydrides, and molecular iodine ($I_2$).

The particular carboxylic acid anhydride used in the process is not critical provided that the carboxylic acid moiety of the anhydride contains at least one α-hydrogen atom. Examples of anhydrides which may be used include those having the formula

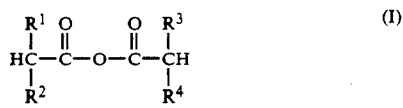 (I)

wherein $R^1$, $R^2$, $R^3$ and $R^4$ are the same or different and each is hydrogen or an unsubstituted or substituted alkyl, cycloalkyl or carbocyclic or heterocyclic aryl radical. Preferred anhydride reactants of formula (I) are those in which $R^1$ and $R^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen and $R^2$ and $R^4$ each is hydrogen or lower alkyl, i.e., alkyl of 1 to about 4 carbon atoms. The use of acetic anhydride is especially preferred.

Examples of the alkyl iodides, α-iodocarboxylic acids and mono-α-iodocarboxylic anhydrides which may be obtained in accordance with our invention include compounds having, respectively, the formulas:

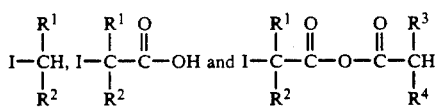

wherein $R^1$, $R^2$, $R^3$ and $R^4$ are defined above.

The process is conducted at elevated temperatures such as temperatures in the range of about 50° C. to 200° C., although temperatures in the range of about 90° C. to 150° C. may be used to give good reaction rates. The process may be conducted in the presence of an inert solvent or diluent such as lower carboxylic acids, trisubstituted carboxylic acids, e.g., pivalic acid, aromatic hydrocarbons and halogenated hydrocarbons, especially iodides, although a solvent normally is neither advantageous nor preferred. The process typically is carried out at ambient pressure although pressures moderately above or below atmospheric may be used.

Examples of the peroxides which may be used in our novel process include hydrogen peroxide; aliphatic peroxides such as dialkyl peroxides, e.g., di-tertiary-butyl peroxide; peracids such as percarboxylic acids, e.g., peracetic and perpropanoic acids; and acyl peroxides (also referred to as diacyl peroxides) such as carboxylic peroxides, e.g., acetyl (diacetyl) peroxide and propionyl (dipropionyl) peroxide. Hydrogen peroxide and peracetic acid are the preferred peroxides. The hydrogen peroxide suitable for use in the process comprises aqueous hydrogen peroxide having a peroxide content of 3 to about 90 weight percent. For economic and safety reasons, the aqueous hydrogen peroxide most suitable for use in the process has a hydrogen peroxide content of about 30 to 70 weight percent.

Normally the amount of peroxide used should be at least 0.5 mole per mole of iodine atoms (I·). Although a very large excess, e.g., up to 200 moles peroxide per mole iodide, may be used, amounts in the range of about 1 to 10 moles peroxide per mole iodine are more typical.

Our novel process can be used for a variety of applications starting with the preparation of the alkyl iodides and α-iodocarboxyl compounds. Additional applications include the recovery of iodine from waste streams, iodine contaminated product effluents, or from iodine containing by-product streams by conversion to forms suitable for reuse (recycle) or use in other chemical processes. For example, one of the primary problems associated with the use of alkyl iodides as alkylating agents on a large scale is the substantial economic burden occasioned by the disposal of the iodine by-product. Our process provides a means for the regeneration of the alkyl iodide by using the appropriate carboxylic anhydride. Alternatively, the iodine by-product can be used to generate the useful α-iodocarboxylic acids.

The process may be performed in a manner to favor the formation of predominantly one product which can be isolated according to conventional procedures. For example, the process may be used to produce primarily alkyl iodides, which normally are more volatile than both the carboxylic anhydrides and mono-α-carboxylic anhydrides, by continuously distilling the alkyl iodide from the reaction mixture as it is formed. Thus, a preferred embodiment of our invention involves the preparation of an alkyl iodide by the steps comprising (1) contacting a mixture of an iodine compound and a carboxylic anhydride with hydrogen peroxide at elevated temperature and (2) removing alkyl iodide vapor from the mixture.

Our novel process is further illustrated by the following examples. Extreme care must be exercised in the addition of aqueous hydrogen peroxide to carboxylic acid anhydrides. Several different analytical techniques were used in determining the iodine-containing components in the reaction mixtures. The iodoacetyl and α-iodopropanoyl contents were established by hydrolysis of the sample with a portion of water equivalent to 20 weight percent of the sample. The hydrolyzed samples were subsequently analyzed using ion chromatography coupled with an electrochemical detector and are reported in terms of the α-iodocarboxylic acid after correction for the quantity of water used in the hydrolysis. Methyl iodide levels were determined by gas chromatography analysis.

EXAMPLE 1

A solution of elemental iodine (8.9 g) in acetic acid (300 g) and acetic anhydride (700 g) was heated to 110° C. and then 30% aqueous hydrogen peroxide (17.8 g) was added in a dropwise fashion with continuous magnetic stirring. Caution! It is important that the addition be carried out slowly in a dropwise fashion as the addition of aqueous hydrogen peroxide to the acetic anhydride-containing solution is, as expected, very exothermic. After the addition was complete, the temperature was maintained for 1 hour and then the reaction mixture was allowed to cool to room temperature and was analyzed for methyl iodide and iodoacetyl content (reported as iodoacetic acid.) Analysis: Methyl iodide: 0.12% by weight, Iodoacetic acid: 1.21% by weight.

EXAMPLE 2

A solution of elemental iodine (9.3 g) in propanoic acid (300 g) and propanoic anhydride (700 g) was heated to 110° C. and then 30% aqueous hydrogen peroxide (17.8 g) was added in a dropwise fashion with continuous magnetic stirring. After the addition was complete, the temperature was maintained at 110° C. for 1 hour and then the reaction mixture was allowed to cool to room temperature. The mixture obtained was analyzed for ethyl iodide and iodopropanoyl content (reported as iodopropanoic acid). Analysis: Ethyl iodide: 0.12% by weight, α-Iodopropanoic acid: 0.29% by weight. (No β-iodopropanoic acid detected.)

EXAMPLE 3

A solution (1 Kg) of methyl iodide in 30 weight percent acetic acid in acetic anhydride was prepared to approximate 100 ppm of iodine. This solution was heated to 125° C. and 30% hydrogen peroxide (2 mL) was added. The temperature was maintained at 125° C. for 1 hour and the solution was allowed to cool to room temperature. Analysis for iodine content indicated that the solution was 76 ppm iodine. The product was then analyzed for methyl iodide and iodoacetyl content (as iodoacetic acid). Analysis: Methyl iodide: 43 ppm, Iodoacetic acid: 16 ppm. (Ratio methyl iodide:Iodoacetic acid (wt./wt.)=2.7)

EXAMPLE 4

This example is identical to Example 3, except that iodoacetic acid is the starting material instead of methyl iodide.

A solution (1 kg) of iodoacetic acid (100 ppm) in 30 weight percent acetic acid in acetic anhydride was heated to 125° C. and 30% hydrogen peroxide (2 mL) was added. The temperature was maintained at 125° C. for 1 hour and the solution was allowed to cool to room temperature. Analysis for iodine content indicated that the solution was 87 ppm iodine. The product was analyzed for methyl iodide and iodoacetyl content (as iodoacetic acid). Analysis: Methyl iodide: 50 ppm, Iodoacetic acid: 23 ppm. (Ratio Methyl Iodide: Iodoacetic acid (wt./wt.)=2.2)

EXAMPLE 5

This example demonstrates the feasibility of using iodoacetone as the iodine compound reactant in the process.

A solution (1 kg) of iodoacetone (83 ppm) in 30 weight percent acetic acid in acetic anhydride was heated to 110° C. and 30% hydrogen peroxide (2 mL) was added. The temperature was maintained at 110° C. for 1 hour and the solution was allowed to cool to room temperature. The product was analyzed for methyl iodide and iodoacetyl content (as iodoacetic acid). Analysis: Methyl iodide: 45 ppm, Iodoacetic acid: 14 ppm.

EXAMPLE 6

A solution (1 kg) of sodium iodide (100 mg) in 30 weight percent acetic acid in acetic anhydride was heated to 110° C. and 30% hydrogen peroxide (2 mL) was added. The temperature was maintained at 110° C. for 1 hour and the solution was allowed to cool to room temperature. The product was analyzed for methyl iodide and iodoacetyl content (as iodoacetic acid). Analysis: Methyl iodide: 58 ppm, Iodoacetic acid: 9 ppm.

EXAMPLE 7

A solution (1 kg) of ethyl iodide (102 mg) in 30 weight percent acetic acid in acetic anhydride was heated to 110° C. and 30% hydrogen peroxide (2 mL) was added. The temperature was maintained at 110° C. for 1 hour and the solution was allowed to cool to room temperature. The product was analyzed for methyl iodide and iodoacetyl content (as iodoacetic acid). Analysis: Methyl iodide: 39 ppm, Iodoacetic acid: 4 ppm.

EXAMPLE 8

This example illustrates the continuous removal of a volatile alkyl iodide to shift the reaction in favor of the formation of an alkyl iodide.

A solution (1 kg) of acetyl iodide (210 ppm) in 30 weight percent acetic acid in acetic anhydride was heated to 90° C. An argon purge was established to continually remove methyl iodide as it was formed. Then 30% hydrogen peroxide (2 mL) was added and the temperature was maintained at 90° C. for 1 hour while continuously removing methyl iodide. The residue of the reaction mixture was allowed to cool to room temperature. Analysis for iodine content indicated that the residue contained only 15 ppm iodine (7% of the initial charge) while the rest had been distilled, presumably as methyl iodide. The remaining material was analyzed for methyl iodide and iodoacetyl content (as iodoacetic acid). The methyl iodide level was measured at 14.5 ppm and iodoacetic acid was undetectable, indicating that about 99% of the iodine had been converted to methyl iodide.

EXAMPLE 9

A solution (1 kg) of hydrogen iodide (113 ppm) in 30 weight percent propanoic acid in propanoic anhydride was heated to 110° C. and then 30% hydrogen peroxide (2 mL) was added and the temperature was maintained at 110° C. for 1 hour. The reaction mixture was allowed to cool to room temperature and was analyzed for ethyl iodide and α-iodopropanoyl content (as α-iodopropanoic acid). Analysis: Ethyl iodide: 56 ppm, α-Iodopropanoic acid: <1 ppm.

The invention has been described in detail with particular reference to preferred embodiments thereof, but it will be understood that variations and modifications may be effected within the spirit and scope of the invention.

We claim:

1. Process for the coproduction of (1) an alkyl iodide and (2) an α-iodocarboxylic acid, a mono-α-iodo-carboxylic anhydride or a mixture thereof which comprises contacting a mixture of an iodine compound and a carboxylic anhydride with a peroxide at an elevated temperature.

2. Process according to claim 1 wherein the iodine compound is selected from molecular iodine, inorganic iodides, carboxylic acid iodides and organic iodine compounds wherein an iodine atom is covalently bonded to a non-aromatic carbon atom and the process is carried out at a temperature of about 50° C. to 200° C.

3. Process according to claim 2 wherein the carboxylic anhydride has the formula

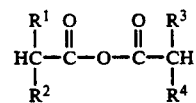

wherein
R$^1$ and R$^3$ each is hydrogen, alkyl of up to about 20 carbon atoms, cyclohexyl, phenyl or phenyl substituted with alkyl of up to 8 carbon atoms, alkoxy of up to 8 carbon atoms, hydroxyl or halogen; and
R$^2$ and R$^4$ each is hydrogen or lower alkyl.

4. Process for the coproduction of (1) an alkyl iodide having the formula

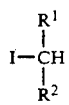

and (2) an α-iodocarboxylic acid having the formula

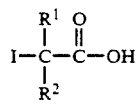

a mono-α-iodocarboxylic anhydride having the formula

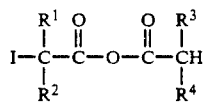

or a mixture thereof which comprises contacting a mixture of (1) an iodine compound selected from molecular iodine, alkali metal and alkaline earth metal iodides, carboxylic acid iodides and alkyl iodides and (2) a carboxylic anhydride having the formula

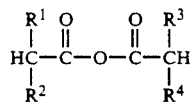

with a peroxide at a temperature of about 50° C. to 200° C, wherein $R^1$ and $R^3$ each is hydrogen, alkyl of up to about 20 carbon atoms, cyclohexyl, phenyl or phenyl substituted with alkyl of up to 8 carbon atoms; and $R^2$ and $R^4$ each is hydrogen or lower alkyl.

5. A process according to claim 4 wherein the process is carried out at a temperature of about 90° C. to 150° C. using about 1 to 10 moles of hydrogen peroxide or peracetic acid per mole of iodine atoms.

6. Process for the preparation of an alkyl iodide having the formula

by the steps comprising

I. contacting a mixture of (1) an iodine compound selected from molecular iodine, alkali metal and alkaline earth metal iodides, carboxylic acid iodides and alkyl iodides and (2) a carboxylic anhydride having the formula

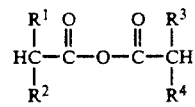

with a peroxide at a temperature of about 50° C. to 200° C. and

II. removing the alkyl iodide as a vapor from the mixture as it is formed, wherein $R^1$ and $R^3$ each is hydrogen, alkyl of up to about 20 carbon atoms, cyclohexyl, phenyl or phenyl substituted with alkyl of up to 8 carbon atoms; and $R^2$ and $R^4$ each is hydrogen or lower alkyl.

7. A process according to claim 6 wherein step I is carried out at a temperature of about 90° C. to 150° C. using about 1 to 10 moles of hydrogen peroxide or peracetic acid per mole of iodine atoms.

8. Process for the coproduction of methyl iodide and mono-α-iodoacetic anhydride which comprises contacting a mixture of (1) an iodine compound selected from molecular iodine, alkali metal and alkaline earth metal iodides, carboxylic acid iodides and alkyl iodides and (2) acetic anhydride with about 1 to 10 moles of hydrogen peroxide or peracetic acid per mole of iodine atoms at a temperature of about 90° C. to 150° C.

9. Process for the preparation of methyl iodide which comprises the steps of

I. contacting a mixture of (1) an iodine compound selected from molecular iodine, alkali metal and alkaline earth metal iodides, carboxylic acid iodides and alkyl iodides and (2) acetic anhydride with about 1 to 10 moles of hydrogen peroxide or peracetic acid per mole of iodine atoms at a temperature of about 90° C. to 150° C. and II. removing the alkyl iodide as a vapor from the mixture as it is formed.

* * * * *